(12) United States Patent
Hofmann

(10) Patent No.: US 7,572,782 B2
(45) Date of Patent: *Aug. 11, 2009

(54) USE OF TARGETED OXIDATIVE THERAPEUTIC FORMULATION IN BONE REGENERATION

(75) Inventor: Robert F. Hofmann, Austin, TX (US)

(73) Assignee: Torquin, LLC, Austin, TX (US)

( * ) Notice: Subject to any disclaimer, the term of this patent is extended or adjusted under 35 U.S.C. 154(b) by 329 days.

This patent is subject to a terminal disclaimer.

(21) Appl. No.: 11/125,773

(22) Filed: May 10, 2005

(65) Prior Publication Data

US 2005/0250755 A1  Nov. 10, 2005

Related U.S. Application Data

(60) Provisional application No. 60/569,554, filed on May 10, 2004.

(51) Int. Cl.
| | |
|---|---|
| A61K 31/555 | (2006.01) |
| A61K 31/535 | (2006.01) |
| A61K 31/405 | (2006.01) |
| A61K 31/135 | (2006.01) |
| A61K 31/12 | (2006.01) |
| A61K 31/075 | (2006.01) |
| A61K 31/045 | (2006.01) |
| A61K 31/02 | (2006.01) |

(52) U.S. Cl. ............ 514/185; 514/236.2; 514/415; 514/652; 514/682; 514/714; 514/724; 514/743

(58) Field of Classification Search .......... 514/185, 514/236.2, 415, 652, 682, 714, 724, 743
See application file for complete search history.

(56) References Cited

U.S. PATENT DOCUMENTS

| | | | |
|---|---|---|---|
| 4,451,480 A | 5/1984 | DeVillez | |
| 4,591,602 A | 5/1986 | DeVillez | |
| 4,983,637 A | 1/1991 | Herman | |
| 5,086,076 A | 2/1992 | Herman | |
| 5,126,376 A | 6/1992 | Herman | |
| 5,190,977 A | 3/1993 | Herman | |
| 5,190,979 A | 3/1993 | Herman | |
| 5,260,342 A | 11/1993 | Herman | |
| 5,270,344 A | 12/1993 | Herman | |
| 5,364,879 A | 11/1994 | Herman | |
| 6,790,463 B2 * | 9/2004 | Hofmann et al. | ............ 424/613 |
| 6,884,797 B2 * | 4/2005 | Hofmann | ............ 514/185 |

FOREIGN PATENT DOCUMENTS

| | | |
|---|---|---|
| WO | WO 02/078622 A2 | 10/2002 |
| WO | WO 03/065996 A2 | 8/2003 |

OTHER PUBLICATIONS

Notification of Transmittal of the International Search Report and the Written Opinion of the International Searching Authority, or the Declaration from the PCT dated May 5, 2006.
Beck-Coon, R.J., et al.; "An In Vivo of the Use of a Nonresorbable Ceramic Hydroxyapatite as an Alloplastic Graft Material in Periapical Surgery"; Oral Surg Med Oral Pathol, vol. 71(4), pp. 483-488, 1991.
Chakraborti, T., et al.; "Oxidant, Mitochondria and Calcium: an Overview"; Cell Signal; vol. 11(2), pp. 77-85, 1999.
Granchi, D., et al.; "Endodontic Cements induce Alterations in the Cell Cycle of an In Vitro Cultured Osteoblasts"; Oral Surg Oral Med Oral Pathol Oral Radiol Endod, vol. 79(3), pp. 359-366, 1995.
Plachot, J.J., et al.; "Mitochondrial Calcium and Bone Mineralization in the Rat Fetus"; Bone Miner, vol. 1(2), pp. 157-166, 1986.
World Health Organization, The Burden of Musculoskeletal Conditions at the Start of the New Millenium, Global Burden of Diseases 2000 Study, 2000. Who Technical Report, Series 919, published 2003.

* cited by examiner

*Primary Examiner*—Kevin E Weddington
(74) *Attorney, Agent, or Firm*—Jackson Walker L.L.P.

(57) ABSTRACT

A pharmaceutical formulation and its use. The pharmaceutical formulation contains peroxidic species or reaction products resulting from oxidation of an alkene, such as geraniol, by an oxygen-containing oxidizing agent, such as ozone; a penetrating solvent, such as dimethylsulfoxide ("DMSO"); a dye containing a chelated metal, such as hematoporphyrin; and an aromatic redox compound, such as benzoquinone. The pharmaceutical formulation is used to effectively stimulate bone regeneration and increase osteoblastic activity in a patient.

22 Claims, No Drawings

USE OF TARGETED OXIDATIVE THERAPEUTIC FORMULATION IN BONE REGENERATION

This application claims priority to U.S. Provisional Patent Application Ser. No. 60/569,554, entitled "Use of Targeted Oxidative Therapeutic Formulation in Bone Regeneration" filed on May 10, 2004, the entire content of which is hereby incorporated by reference.

BACKGROUND

The present invention relates to a composition containing peroxidic species or oxidation products, its method of preparation, and its use. More specifically, the invention relates to a pharmaceutical composition or formulation which contains: peroxidic species or reaction products resulting from oxidation of an olefinic compound, in a liquid form or in a solution, by an oxygen-containing oxidizing agent; a penetrating solvent; a dye containing a chelated metal; and an aromatic redox compound. The invention also relates to the preparation of the pharmaceutical formulation and its use in bone regeneration.

Musculoskeletal and limb trauma are a serious economic burden in both developed and developing parts of the world. Longer life expectancy and an increasing number of elderly population groups have led to an increasing incidence of musculoskeletal disease worldwide. In the US alone, an estimate of the total costs related to musculoskeletal conditions amounts to more than $250 billion per year (World Health Organization, 2000). As the number of individuals over the age of 65 years increases, the total annual medical costs of these injuries will continue to increase. The direct burden includes costs and fees associated with hospital and nursing home care, physician and other professional services, rehabilitation, community-based services, the use of medical equipment, prescription drugs, local rehabilitation, home modifications, and insurance administration. Direct costs do not account for the long-term consequences of these injuries, such as disability, decreased productivity, lost wages, and diminished quality of life.

In addition, current techniques and methods to accelerate bone repair and implant fixation suffer from notable disadvantages. The bone cements and sealers traditionally applied may adversely affect osteoblast recovery. Studies have shown that root canal sealers hamper the periapical healing processes by inhibiting osteoblastic cell proliferation (Granchi, et al., 1995). Furthermore, despite its excellent biocompatibility, hydroxyapatite appears to retard osteogenesis by its physical presence (Beck-Coon, et al., 1991). Macrophages and osteoblasts also react adversely to metals such as aluminum, lead, and cadmium.

Chronic dental infections and root canal procedures may also be risk factors in the development of distal pathological conditions, including atherosclerosis. Complete eradication of anaerobic infection of periodontal bone is difficult, despite antibiotics, root canal therapy, and surgical drainage. Closure of infected "dead space" by drainage, macrophage initiation, and osteoblastic bone repair all need to occur to prevent a focus for distant infection.

Macrophagic and osteoblastic cell functions depend upon a correctly functioning intracellular relationship between mitochondria, microfilaments, and peroxidation chemistry. Mitochondria are also important participants in cellular calcium dynamics and regulate the supply of release-competent secretory granules (Chakraborti, et al., 1999). Evidence suggests that osteoblasts possess calcium phosphate in the form of granules within their mitochondria (Plachot, et al., 1986). Furthermore, the induction of osteoblast function in bone repair seems to require proper mitochondrial outer membrane function. Intracellular controlled peroxidation is a known trigger of osteoblast transformation and calcium secretion in bone repair.

Ozone is a triatomic gas molecule and an allotropic form of oxygen. It may be obtained by means of an electrical discharge or intense ultraviolet light through pure oxygen. The popular misconception that ozone is a serious pollutant, the "free radical" theory of disease, and the antioxidant supplement market have comprehensibly prejudiced medical orthodoxy against its use as a treatment. Ozone therapy, however, is a misnomer. Ozone is an extremely reactive and unstable gas with mechanisms of action directly related to the by-products that it generates through selective interaction with organic compounds present in the plasma and in the cellular membranes. The selective reaction of ozone with unsaturated olefins occurs at the carbon-carbon double bond, generating ozonides. Ozone is toxic by itself, and its reaction products, ozonides, are unstable and are not therapeutic by themselves.

Hydrogen peroxide ($H_2O_2$), discovered in 1818, is present in nature in trace amounts. Hydrogen peroxide is unstable and decomposes violently (or foams) when in direct contact with organic membranes and particulate matter. Light, agitation, heating, and iron all accelerate the rate of hydrogen peroxide decomposition in solution. Hydrogen peroxide by direct contact ex vivo kills microbes that have low levels of peroxide-destroying enzymes, such as the catalases. However, there is no bactericidal effect when hydrogen peroxide is infused into the blood of rabbits infected with peroxide-sensitive E. coli. Moreover, increasing the concentration of peroxide ex-vivo in rabbit or human blood containing E. coli produces no evidence of direct bactericidal activity. The lack of effect of high concentrations of hydrogen peroxide is directly related to the presence of the peroxide-destroying enzyme catalase in the host animal's blood. To have any effect, high concentrations of hydrogen peroxide have to be in contact with the bacteria for significant periods of time. Large amounts of hydrogen peroxide-destroying enzymes, such as catalase, normally present in the blood make it impossible for peroxide to exist in blood for more than a few seconds. Thus, hydrogen peroxide introduced into the blood stream by injection or infusion does not directly act as an extracellular germicide in blood or extracellular fluids.

However, hydrogen peroxide does participate in the bactericidal processes of activated macrophage cells. Activated macrophage cells are drawn to the site of infection, attach to the infectious organism, and ingest it. The killing of the organisms takes place inside the macrophage cell by hydrogen peroxide. Hydrogen peroxide oxidizes cellular chloride to the chlorine dioxide free radical, which destabilizes microbial membranes and, if persistent, induces apoptosis or cellular suicide. The critical therapeutic criteria for intracellular peroxidation are the selective delivery, absorption and activation of peroxidic carrier molecules into only diseased macrophages, which are believed to be incapable of upgraded catalase and glutathione reductase activity. Infused hydrogen peroxide is a generalized poison whereas targeted intracellular peroxidation is a selective therapeutic tool.

Macrophage cells play critical roles in immunity, bone calcification, vision, neural insulation (myelinization), detoxification, pump strength, and clearance of toxins from the body, depending upon their site of localization. The energy requirements of macrophages are met by intracellular structures called mitochondria. Mitochondria are often structurally associated with the microfilament internal cytoarchitecture. The folded internal layer of the mitochondria creates the high-energy molecule ATP, while the outer layer contains cytochromes and electron recycling molecules that generate peroxides. The outer layers of mitochondria are susceptible to toxic blockade or damage by endotoxins, mycotoxins, virally encoded toxins, drugs, heavy metals, and pesticides. When the peroxidation function of mitochondria is blocked, the filament architecture of the cell tends to cross-link, generating incorrect signals, incompetence, inappropriate replication, or premature cell death.

U.S. Pat. No. 4,451,480 to De Villez teaches a composition and method for treating acne. The method includes topically treating the affected area with an ozonized material derived from ozonizing various fixed oil and unsaturated esters, alcohols, ethers and fatty acids.

U.S. Pat. No. 4,591,602 to De Villez shows an ozonide of Jojoba used to control microbial infections.

U.S. Pat. No. 4,983,637 to Herman discloses a method to parenterally treat local and systemic viral infections by administering ozonides of terpenes in a pharmaceutically acceptable carrier.

U.S. Pat. No. 5,086,076 to Herman shows an antiviral composition containing a carrier and an ozonide of a terpene. The composition is suitable for systemic administration or local application.

U.S. Pat. No. 5,126,376 to Herman describes a method to topically treat a viral infection in a mammal using an ozonide of a terpene in a carrier.

U.S. Pat. No. 5,190,977 to Herman teaches an antiviral composition containing a non-aqueous carrier and an ozonide of a terpene suitable for systemic injection.

U.S. Pat. No. 5,190,979 to Herman describes a method to parenterally treat a medical condition in a mammal using an ozonide of a terpene in a carrier.

U.S. Pat. No. 5,260,342 to Herman teaches a method to parenterally treat viral infections in a mammal using an ozonide of a terpene in a carrier.

U.S. Pat. No. 5,270,344 to Herman shows a method to treat a systemic disorder in a mammal by applying to the intestine of the mammal a trioxolane or a diperoxide derivative of an unsaturated hydrocarbon which derivative is prepared by ozonizing the unsaturated hydrocarbon dissolved in a non-polar solvent.

U.S. Pat. No. 5,364,879 to Herman describes a composition for the treatment of a medical condition in a mammal, the composition contains a diperoxide or trioxolane derivative of a non-terpene unsaturated hydrocarbon which derivative is prepared by ozonizing below 35° C. the unsaturated hydrocarbon in a carrier.

Despite the reports on the use of terpene ozonides for different medical indications, terpene ozonides display multiple deficiencies. For example, ozonides of monoterpene, such as myrcene and limonene, flamed out in the laboratory. Consequently, they are extremely dangerous to formulate or store.

Thus, there is a need for a safe and effective pharmaceutical formulation or composition utilizing reaction products from the oxidation of an alkene compound. What is also needed is a method for stimulating mitochondrial defenses against free radical formation and effectively treating individuals affected with cancers such as lymphoma.

SUMMARY

This invention is directed to pharmaceutical formulations comprising peroxidic species or reaction products resulting from oxidation of an unsaturated organic compound, in a liquid form or in a solution, by an oxygen-containing oxidizing agent; a penetrating solvent; a chelated dye; and an aromatic redox compound. In one embodiment of the pharmaceutical formulation, the essential components include the peroxidic products formed by ozonolysis of an unsaturated alcohol, a stabilizing solvent, metalloporphyrin, and quinone. This invention is also directed to use of the pharmaceutical formulation to treat cancer.

The peroxidic species or reaction products are preferably formed through the reaction of an alkene and ozone. It is generally accepted that the reaction between an alkene and ozone proceeds by the Criegee mechanism. According to this mechanism, shown in Scheme 1 below, the initial step of the reaction is a 1,3-dipolar cycloaddition of ozone to the alkene to give a primary ozonide (a 1,2,3-trioxalane). The primary ozonide is unstable, and undergoes a 1,3-cycloreversion to a carbonyl compound and a carbonyl oxide. In the absence of other reagents or a nucleophilic solvent, this new 1,3-dipole enters into a second 1,3-dipolar cycloaddition to give the "normal" ozonide, a 1,2,4-trioxalane.

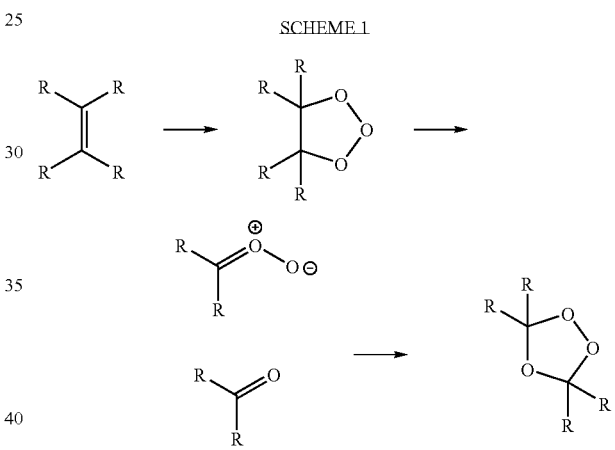

SCHEME 1

In a side reaction, the carbonyl oxide can enter into a dimerization to give a peroxidic dimer, the 1,2,4,5-tetraoxane, shown in Scheme 2 below.

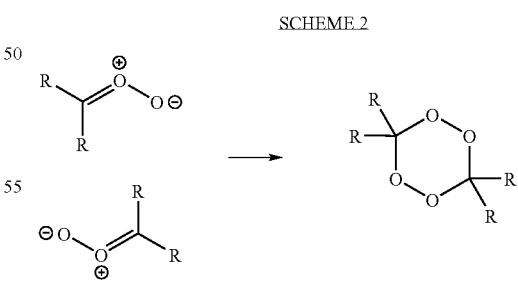

SCHEME 2

The carbonyl oxide is a strongly electrophilic species, and in the presence of nucleophilic species (e.g. alcohols or water), it undergoes facile nucleophilic addition to give a 1-alkoxyhydroperoxide, shown in Scheme 3 below. Under certain conditions, the 1-alkoxyhydroperoxide can undergo further reaction to give carboxylic acid derivatives.

SCHEME 3

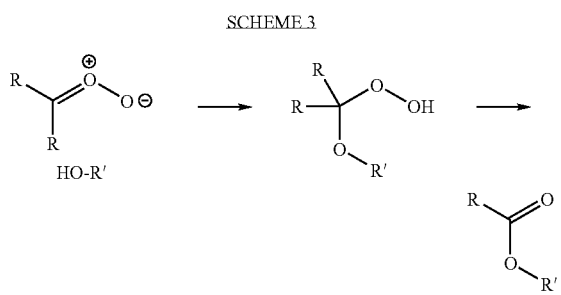

Again, not wanting to be bound by theory, it is believed that during the ozonolysis of the alcohol-containing alkene in the present invention, it is reasonable to expect that three major types of peroxidic products will be present: the normal ozonide, the carbonyl tetraoxane dimer, and the 1-alkoxyhydroperoxide. In the presence of water, some of these peroxidic products may also lead to the presence of organic peracids in the crude product mixture.

The present invention also involves the use of a penetrating solvent such as dimethylsulfoxide ("DMSO") to "stabilize" the initial products of the ozonolysis. Similarly, not wanting to be bound by any theory, it is believed that the stabilization is most likely a simple solvation phenomenon. However, DMSO is known to be a nucleophile in its own right. Its participation is also possible as a nucleophilic partner in stabilizing reactive species (for example, as dimethylsulfoxonium salts). The stabilized peroxidic molecule and the penetrating solvent of the current pharmaceutical formulation are made from components generally regarded as safe ("GRAS").

Another component of the pharmaceutical formulation is a chelated dye, such as a porphyrin. The propensity of metalloporphyrins to sensitize oxygen under photochemical excitation is well documented, as is the propensity of ferroporphyrins and copper porphyrins to bind oxygen-containing systems.

A further component of the pharmaceutical formulation is an aromatic redox compound, such as a quinone.

Although not wanting to be bound by any theory, it is postulated that the preferred pharmaceutical formulation is a combination of biochemical agents that induce recycling autocatalytic oxidation in infected or dysplastic macrophages. The pharmaceutical formulation stimulates targeted apoptosis (cell suicide) through unopposed peroxidation. Thus, the pharmaceutical formulation creates therapeutic effects in a number of seemingly disparate mitochondria-based macrophagic diseases. In particular, the pharmaceutical formulation has been shown to accelerate bone re-growth and healing of periapical dental abscesses, periodontal lesions, and compound fractures. The pharmaceutical formulation is effective at stimulating osteobastic regenerative activity. These results indicate its effectiveness at bone regeneration.

DETAILED DESCRIPTION OF PREFERRED EMBODIMENTS

The current invention pertains to pharmaceutical formulations comprising peroxidic species or reaction products resulting from oxidation of an unsaturated organic compound, in a liquid form or in a solution, by an oxygen-containing oxidizing agent; a penetrating solvent; a chelated dye; and an aromatic redox compound. The pharmaceutical formulations may be used to stimulate bone regeneration and osteoblastic activity in patients affected with bone injuries such as abscesses, lesions, fibromas, and fractures. In one embodiment of the present invention, the essential components of the pharmaceutical formulation include the peroxidic products formed by ozonolysis of an unsaturated alcohol, a stabilizing solvent, metalloporphyrin, and quinone.

The unsaturated organic compound, which may also be an unsaturated olefinic hydrocarbon, of the pharmaceutical formulation can be an alkene without a hydroxyl group, or a hydroxyl-containing alkene. Preferably, the alkene has less than about 35 carbons. The alkene without a hydroxyl group may be an open-chain unsaturated hydrocarbon, a monocyclic unsaturated hydrocarbon, or a bicyclic unsaturated hydrocarbon. The hydroxyl-containing alkene can be an open-chain unsaturated alcohol, a monocyclic unsaturated alcohol, or a bicyclic unsaturated alcohol. The alkene may also be contained in a fixed oil, an ester, a fatty acid, or an ether.

Usable unsaturated olefinic hydrocarbons may be unsubstituted, substituted, cyclic or complexed alkenes, hydrazines, isoprenoids, steroids, quinolines, carotenoids, tocopherols, prenylated proteins, or unsaturated fats. The preferred unsaturated hydrocarbons for this invention are alkenes and isoprenoids.

Isoprenoids are found primarily in plants as constituents of essential oils. While many isoprenoids are hydrocarbons, oxygen-containing isoprenoids also occur such as alcohols, aldehydes, and ketones. In a formal sense, the building block of isoprenoid hydrocarbons may be envisaged as the hydrocarbon isoprene, $CH_2=C(CH_3)-CH=CH_2$, although it is known that isoprene itself is an end-product of isoprenoid biosynthesis and not an intermediate. Isoprenoid hydrocarbons are categorized by the number of isoprene ($C_5H_8$) units they contain. Thus, monoterpenes have 2, sesquiterpenes have 3, diterpenes have 4, sesterterpenes have 5, triterpenes have 6, and tetraterpenes have 8 isoprene units, respectively. Tetraterpenes are much more commonly regarded as carotenoids.

Limonene and pinene are examples of a monoterpene. Farnesol and nerolidol are examples of a sesquiterpene alcohol. Vitamin $A_1$ and phytol are examples of a diterpene alcohol while squalene is an example of a triterpene. Provitamin $A_1$, known as carotene, is an example of a tetraterpene. Geraniol, a monoterpene alcohol, is liquid in both its oxygen bound and normal states and is safe to living cells.

Preferred unsaturated hydrocarbons for the pharmaceutical formulation include alkene isoprenoids, such as myricene, citrillene, citral, pinene, or limonene. Preferred unsaturated hydrocarbons also include linear isoprenoid alcohols with two to four repeating isoprene groups in a linear chain, such as terpineol, citronellol, nerol, phytol, menthol, geraniol, geranylgeraniol, linalool, or farnesol.

The unsaturated organic compound may be linear, branched, cyclic, spiral, or complexed with other molecules in its configuration. The unsaturated organic compound may naturally exist in a gaseous liquid or solid state prior to binding with the oxidizing agent.

An open-chain unsaturated hydrocarbon can be: $C_nH_{2n}$, one double bond, n=2-20; $C_nH_{2n-2}$, two double bonds, n=4-20; $C_nH_{2n-4}$, three double bonds, n=6-20; $C_nH_{2n-6}$, four double bonds, n=8-20; $C_{25}H_{40}$, sesterterpene hydrocarbon; or $C_{30}H_{48}$, triterpene hydrocarbon.

A monocyclic unsaturated hydrocarbon can be: $C_nH_{2n-2}$, one double bond and one ring, n=3-20; $C_nH_{2n-4}$, two double bonds and one ring, n=5-20; $C_nH_{2n-6}$, three double bonds and one ring, n=7-20; $C_{25}H_{40}$, sesterterpene hydrocarbon; or $C_{30}H_{48}$, triterpene hydrocarbon.

A bicyclic unsaturated hydrocarbon can be: $C_nH_{2n-4}$, one double bond and two rings, n=4-20; $C_nH_{2n-6}$, two double bonds and two rings, n=6-20; $C_{25}H_{40}$, sesterterpene hydrocarbon; or $C_{30}H_{48}$, triterpene hydrocarbons.

An open-chain unsaturated alcohol can be: $C_nH_{2n}O_m$, one double bond, n=3-20, m=1-4; $C_nH_{2n-2}O_m$, two double bonds, n=5-20, m=1-4; $C_nH_{2n-4}O_m$, three double bonds, n=7-20, m=1-4; $C_nH_{2n-6}O_m$, four double bonds, n=9-20, m=1-4; $C_{25}H_{40}O_m$, m=1-4, sesterterpene alcohols; or $C_{30}H_{48}O_m$, m=1-4, triterpene alcohols.

A monocyclic unsaturated alcohol can be: $C_nH_{2n-2}O_m$, one double bond and one ring, n=3-20, m=1-4; $C_nH_{2n-4}O_m$, two double bonds and one ring, n=5-20, m=1-4; $C_nH_{2n-6}O_m$, three double bonds and one ring, n=7-20, m=1-4; $C_{25}H_{40}O_m$, m=1-4, sesterterpene alcohols; or $C_{30}H_{48}O_m$, m=1-4, triterpene alcohols.

A bicyclic unsaturate alcohol can be: $C_nH_{2n-4}O_m$, one double bond and two rings, n=5-20, m=1-4; $C_nH_{2n-6}O_m$, two double bonds and two rings, n=7-20, m=1-4; $C_{25}H_{40}O_m$, m=1-4, sesterterpene alcohols; or $C_{30}H_{48}O_m$, m=1-4, triterpene alcohols.

Based on the total weight of the pharmaceutical formulation, the alkene can vary from about 0.001% to about 30%, preferably from about 0.1% to about 5.0%, and more preferably from about 0.5% to about 3.0%.

The oxygen-containing oxidizing agent of the pharmaceutical formulation, which oxidizes the unsaturated hydrocarbon, may be singlet oxygen, oxygen in its triplet state, superoxide anion, ozone, periodate, hydroxyl radical, hydrogen peroxide, alkyl peroxide, carbamyl peroxide, benzoyl peroxide, or oxygen bound to a transition element, such as molybdenum (e.g. $MoO_5$).

The preferred method to bind "activated oxygen" to intact an isoprenoid alcohol, such as geraniol, is by ozonation at temperatures between 0-20° C. in the dark in the absence of water or polar solvent. The geraniol "ozonides" are then dissolved and stabilized in 100% DMSO in the dark to prevent premature breakdown of the products. Although not wanting to be bound by any theory, it is believed that the catalytic breakdown of the tetraoxane peroxidic dimer byproduct of geraniol ozonation, which is not an ozonide, occurs inside of cells in the presence of superoxide anion. The final reactive therapeutic agents released are hydrogen peroxide and acetic acid.

The pharmaceutical formulation also utilizes a penetrating solvent. The penetrating solvent, which stablizes the oxygen-bound unsaturated hydrocarbon, may be an emollient, a liquid, a liposome, a micelle membrane, or a vapor. Usable penetrating solvents include aqueous solution, fats, sterols, lecithins, phosphatides, ethanol, propylene glycol, methylsulfonylmethane, polyvinylpyrrolidone, pH-buffered saline, and dimethylsulfoxide ("DMSO"). The preferred penetrating solvents include DMSO, polyvinylpyrrolidone, and pH-buffered saline. The most preferred penetrating solvent is DMSO.

Based on the total weight of the pharmaceutical formulation, the penetrating solvent can vary from about 50% to about 99%, preferably from about 90% to about 98%, and more preferably from about 95% to about 98%.

The "stabilized" peroxidic molecule and its penetrating solvent have been made from components currently used in production regulated by the Food and Drug Administration ("FDA"). These ingredients are the subject of Drug Master Files, Drug Monographs, are found in the USP/NF, or are Generally Recognized As Safe ("GRAS").

Another component of the pharmaceutical formulation is a chelated dye. The dye preferably contains a chelated divalent or trivalent metal, such as iron, copper, manganese tin, magnesium, or strontium. The preferred chelated metal is iron. The propensity of chelated dyes such as metalloporphyrins to sensitize oxygen under photochemical excitation is well documented, as is the propensity of ferroporphyrins and copper porphyrins to bind oxygen-containing systems. Usable dyes include natural or synthetic dyes. Examples of these dyes include porphyrins, rose bengal, chlorophyllins, hemins, porphins, corrins, texaphrins, methylene blue, hematoxylin, eosin, erythrosin, flavinoids, lactoflavin, anthracene dyes, hypericin, methylcholanthrene, neutral red, phthalocyanine, fluorescein, eumelanin, and pheomelanin. Preferred dyes can be any natural or synthetic porphyrin, hematoporphyrin, chlorophyllin, rose bengal, their respective congeners, or a mixture thereof. The most preferred dyes are mixtures of hematoporphyrin and rose bengal, and mixtures of hematoporphyrin and chlorophyllin. The dye may be responsive to photon, laser, ionizing radiation, phonon, electrical cardiac impulse, electroporation, magnetic pulse, or continuous flow excitation.

Based on the total weight of the pharmaceutical formulation or composition, the dye can vary from about 0.1% to about 30%, preferably from about 0.5% to about 5%, and more preferably from about 0.8% to about 1.5%.

A further component of the pharmaceutical formulation is an aromatic redox compound, such as a quinone. The aromatic redox compound may be any substituted or unsubstituted benzoquinone, naphthoquinone, or anthroquinone. Preferred aromatic redox compounds include benzoquinone, methyl-benzoquinone, naphthoquinone, and methyl-naphthoquinone. The most preferred aromatic redox compound is methyl-naphthoquinone.

Based on the total weight of the pharmaceutical formulation, the aromatic redox compound can vary from about 0.01% to about 20.0%, preferably from about 0.1% to about 10%, and more preferably from about 0.1% to about 0.5%.

The pharmaceutical formulation is also preferably activated by an energy source or an electron donor. Useful electron donors include NADH, NADPH, an electrical current, ascorbate or ascorbic acid, and germanium sesquioxide. Preferred electron donors include ascorbate and germanium sesquioxide. The most preferred electron donor is ascorbic acid in any salt form.

Based on the total weight of the pharmaceutical formulation, the electron donor can vary from about 0.01% to about 20%, preferably from about 1% to about 10%, and more preferably from about 1% to about 5%.

In order to obtain a biological effect in vivo, the pharmaceutical formulation is preferably infused as an ozonolysis-generated peroxidic product of an unsaturated hydrocarbon, rather than an ozonide, in conjunction with a superoxide generating chelated dye and an aromatic quinone. The unsaturated hydrocarbon product, or peroxidic dimer molecule, should be stabilized in a non-aqueous stabilizing solvent and should be capable of penetrating lipid membranes.

Researchers of energetically activated dye therapy have long known that the superoxide generating dye and the aromatic redox compound preferentially absorb into infected and dysplastic cells, which are typically also catalase deficient. Without wanting to be bound by theory, the catalase-induced destruction of peroxide should be overwhelmed in the target cells either naturally or by the pharmaceutical formulation. The peroxidic dimer should also be activated by the superoxide generating dye, initiating electron donation to the dimer and causing the release of hydrogen peroxide and acetic acid intracellularly. The electronic activation of the dye does not always require light, but rather may occur through small electrical pulses provided by, for example, a heart pulse. The peroxidation reaction within the infected macrophage then tends to destroy the prenylated protein linkage of microtubules within the cell, to destroy the infecting toxin, or to induce apoptosis of the macrophage host cell.

The pharmaceutical formulation is a combination of stable ingredients. These ingredients may preferably be stored as dry solid ingredients and liquid ingredients in separate containers, which are then mixed at the site of use. The dry solid ingredients preferably comprise the chelated dye and the aromatic redox compound. The liquid ingredients preferably comprise the peroxidic species or reaction products resulting from oxidation of the unsaturated hydrocarbon by the oxygen-containing active agent, along with the penetrating solvent. Administration is preferably intravenously. The reconstituted product preferably may be administered intravenously as a concentrate diluted in saline. Endodontic, direct intraosseous, intra-articular, topical, intraperitoneal and intrathecal deliveries are also possible routes for administration. Intramuscular injection is not preferred, as it has a tendency to produce local irritation.

Administration of the pharmaceutical formulation in vivo is effective in treating viruses and symptoms of viruses in affected patients. In particular, the pharmaceutical formulation stimulates accelerated healing and bone re-growth in dental abscesses, bone lesions, and fractures. The pharmaceutical formulation causes increased osteoblastic activity and is effective at bone regeneration.

EXAMPLE 1

Ozonolysis of an Unsaturated Hydrocarbon

Ozonolysis of an alkene may be carried out either in a solvent or neat. In either case, the cooling of the reaction mixture is critical in avoiding explosive decomposition of the peroxidic products of the reaction.

The following general procedure is typical for the ozonolysis of a liquid alkene.

A 1-liter flask fitted with a magnetic stirrer is charged with the alkene (2 moles), and the apparatus is weighed. The flask is surrounded by a cooling bath (ice-water or ice-salt). Once the contents are cooled below 5° C., stirring is begun and a stream of ozone in dry oxygen (typically 3% ozone) is passed through the mixture. It is advantageous to disperse the ozonated oxygen through a glass frit, but this is not necessary for a stirred solution. Periodically, the gas stream is stopped, and the reaction flask is weighed or the reaction mixture is sampled. The gas stream is then re-started.

Once the mass of the reaction flask shows sufficient weight gain, or once the proton magnetic resonance ("$H^1$ NMR") spectrum of the reaction mixture shows the desired reduction in the intensity of the olefinic proton resonances (usually about 50%), the gas flow is stopped.

The ozonolysis may be carried out as above, substituting a solution of the alkene in a solvent non-reactive towards ozone such as saturated hydrocarbons or chlorinated hydrocarbons. The ozonolysis may also be carried out as above, with or without solvent, substituting an alkenol for the alkene without affecting the reaction in any substantive manner.

The reaction mixture is then poured slowly into the cooled penetrating solvent.

EXAMPLE 2

Preparation of the Pharmaceutical Formulation

A preferred pharmaceutical formulation of the present invention was prepared as follows:
(1) Sparging an ozone/pure oxygen gas mixture of 120 mg/L up through an alkadiene alcohol, 3,7-dimethyl-2, 6-octadien-1-ol (geraniol), at 1 Liter of gas per hour;
(2) Maintaining the temperature of the reaction around 5° C.;
(3) Removing small aliquots of reaction product hourly and measuring by $H^1$ NMR the formation of the peroxidic species or reaction products;
(4) Stopping the reaction when more than about 50% of the available unsaturated bonds have been reacted;
(5) Diluting the product mixture with dimethylsulfoxide (1:10) to give a solution or dispersion;
(6) Prior to use in the target biological system, a mixture of hematoporphyrin, rose bengal, and methyl-naphthoquinone dry powders was added to the solution or dispersion in sufficient quantity to create a concentration of 20 micromolar of each component dispersed therein when delivered to the target biological system by saline intravenous infusion. Optionally, ascorbate could be added to the formulation prior to use.

EXAMPLE 3

Examples of the Pharmaceutical Formulation

Two preferred formulations are as follows:

| A. | |
|---|---|
| WEIGHT % | INGREDIENT |
| 0.54* | Tetraoxane dimer of acetal peroxide from ozonation of geraniol |
| 98.00 | DMSO |
| 0.83 | Hematoporphyrin |
| 0.24 | Methylnaphthoquinone |
| 0.39 | Rose Bengal |

*Determined by mass spectroscopy.

| B. | |
|---|---|
| WEIGHT % | INGREDIENT |
| 0.54* | Tetraoxane dimer of acetal peroxide from ozonation of geraniol |
| 98.00 | DMSO |
| 0.83 | Hematoporphyrin |
| 0.24 | Methylnaphthoquinone |
| 0.39 | Chlorophyllin Sodium-Copper Salt |

*Determined by mass spectroscopy.

EXAMPLE 4

Treatment of Endodontic Bone Abscesses

Fifteen patients with periapical bone abscesses participated in a study to determine the effects of the pharmaceutical formulation in bone repair and healing after endodontic treatment. Twelve patients were treated with endodontic debridement, augmented with examples of the pharmaceutical formulation. Three were untreated and served as conventional controls. The treated patients had their infected teeth opened and debrided. An example of the pharmaceutical formulation having Formulation A from Example 3 above was instilled into the canals and periapical bone at a concentration of 1 cc pharmaceutical formulation to 10 cc saline, along with 0.2 ml $Ca(OH)_2$. Radiographic documentation of the periapical abscess was performed prior to and six to eight weeks following endodontic treatment. Controls were treated by non-augmented endodontic debridement. The debridement was followed by obturation, gutta percha canal filling, and intermediate restorative material ("IRM") sealing in both treated and control patients.

Treated Subjects

A 79 year-old male had a one-month history of an infected fistula, through the lateral gingival area of a tooth (location 2). An initial radiograph revealed an extensive abscess in the periapical bone above the tooth. The subject underwent endodontic surgery, which released purulent exudate from the root canals and the fistula. The tooth and bone were treated with augmented pulp debridement initially. The secondary debridement and root canal filling with gutta percha was accomplished three weeks later. Fourteen days later, the fistula had resolved and a follow-up radiograph showed resolution of the periapical abscess with rapid bone regrowth.

A 50 year-old male presented with a one-month history of cold temperature sensitivity in a tooth (location 19). That tooth previously had been treated endodontically ten years prior with a partial fill of the root canals. An initial radiograph demonstrated moderate periapical radiolucency around the anterior root. The patient underwent re-operation with augmented endodontic surgery as described above. All symptoms resolved within 48 hours. Completion of the endodontic procedure was accomplished three weeks later with gutta percha filling. A follow-up radiograph demonstrated near resolution of the periapical radiolucency with increased bone density.

A 43 year-old female presented with a two-month history of facial swelling and pain with percussion sensitivity at a tooth (location 6). An initial radiograph demonstrated periapical radiolucency around the root of the tooth. The patient underwent augmented endodontic surgery as described above. The facial swelling resolved within two weeks. Completion of the endodontic procedure was accomplished three weeks later with gutta percha filling. A follow-up radiograph demonstrated near resolution of the periapical radiolucency with increased bone density.

A 50 year-old female presented with facial swelling pain over a tooth (location 19). The tooth had been endodontically treated within the previous three months without success. The patient also had undergone radioactive iodine therapy for thyroid cancer six months prior. An initial radiograph demonstrated the previous incomplete filling and the extensive periapical radiolucency about the posterior root. The patient underwent augmented endodontic surgery as described above. Bacterial culture of the purulent debris showed *Neisseria* and Alpha *Streptococcus*. After treatment, the facial swelling resolved within four days. Completion of the endodontic procedure was accomplished six weeks later with gutta percha filling. A follow-up radiograph demonstrated near resolution of the periapical radiolucency with increased bone density.

A 59 year-old female presented with a three-month history of a fistulous tract over the palatal apical area of a tooth (location 2). The patient had periodontal surgery in the area four months earlier. Cultures of the debris removed from the tract showed Beta *Streptococcus, Enterococcus* (Group D), and *Fusobacterium varium*. The tooth and bone were treated with augmented endocontic surgery as described above. A temporary restoration was placed and the root canal was completed six weeks later. At that time the fistula appeared to be healing. Three weeks later, the area showed complete healing.

A 43 year-old female presented with an infected maxillary bicuspid (location 13). A radiograph revealed a thickened periodontal ligament ("PDL"), especially on the mesial side of the entire root at the apex, possibly a fractured tooth. Augmented endodontic surgery was performed as described above. The patient was subjectively improved within 24 hours and was asymptomatic at the completion appointment one month later. The PDL had a noticeable reduction in thickness, especially on the mesial side, within six weeks.

A 47 year-old female presented with an infected tooth (location 14). The upper left area was swollen, causing pain in the maxillary left quadrant. Augmented endodontic surgery was performed as described above. The pain and swelling disappeared one day after the appointment. Within one month the patient was asymptomatic and the obturation with filling of the canal spaces was uneventful.

A 50 year-old male presented with pain in the lower left mandible. Examination determined that two teeth were responsible. One (location 18) suffered from irreversible pulpitis and another (location 19) was infected at the site of a previous root canal and showed periapical radiolucency at its distal root. Both teeth were treated with the augmented endodontic procedure described above. The next day, the patient reported no pain since the surgery, without analgesic or anti-inflammatory medication. The radiolucency on the distal root of the second tooth had disappeared two months later, when the treatment procedures were completed, and the teeth remained asymptomatic.

A 31 year-old female presented with chronic cementitis and periodontitis in a tooth (location 19) that had been undergoing treatment for over two months. A radiograph revealed bone radiolucency at the root end. The tooth was re-treated with the augmented endodontic procedure described above. The subject reported notable pain relief within a few days. The area was asymptomatic at one month, when the root canal procedure was completed conventionally. Radiographs taken six weeks later showed the bone abscess to be healed.

A 76 year-old female presented with occasional pain over a tooth (location 21). The medical history of the patient revealed previous heart attack, cancer, and antibiotic allergies. A radiograph showed periapical radiolucency and calcification of the dental canals. The tooth was re-treated with the augmented endodontic procedure described above. Pain was relieved within one day. Radiographs at the one-month session demonstrated disappearance of the bone abscess radiolucency.

A 40 year-old female presented with pain and a periapical bone abscess around a tooth (location 18), despite endodontic treatment several years prior. The tooth was re-treated with the augmented endodontic procedure described above. Completion of the entire treatment procedure occurred six weeks later. At six weeks, radiographs revealed marked improvement and some resolution of the periapical abscess lesion.

An 18 year-old female suffered from a periapical bone abscess lesion on the mesial root of a tooth (location 19). The pulp extracted during endodontic treatment was necrotic. The tooth was re-treated with the augmented endodontic procedures described above. Final treatment was accomplished in a conventional manner with gutta percha and zinc oxide, sealed over with IRM. A radiograph at eight weeks revealed improvement and some resolution of the periapical abscess lesion.

Control Subjects

A 58 year-old male presented with a tooth (location 13) having a history of periodontal disease. Its pulp was necrotic. A radiograph revealed a periapical bone abscess lesion. Conventional endodontic treatment was accomplished with interim dressing of $Ca(OH)_2$. Treatment was completed six weeks later. The tooth was still mildly symptomatic and the bone abscess was still present on the radiograph, perhaps slightly larger.

A 47 year-old male had a tooth (location 10) previously restored with a crown and bridge, which manifested severe resorption of the periapical bone with chronic pain. Conventional endodontic treatment was accomplished with interim dressing of $Ca(OH)_2$. Treatment and gutta percha root canal filling was completed six months later. The tooth was still mildly symptomatic and the periapical bone defect was still present on a radiograph one year later.

A 49 year-old female presented with a fractured tooth (location 19) that had caused pain for one year, despite restoration. An initial radiograph showed a dentinal fracture and periapical bone abscess. Conventional endodontic treatment was accomplished with interim dressing of $Ca(OH)_2$. Obturation and gutta percha root canal filling was completed seven weeks later. The tooth was mildly symptomatic and the periapical bone defect was still present on a radiograph taken eight months later.

These results, including a comparison of treated and control subjects, indicate that the pharmaceutical formulation is effective at treating endodontic bone abscesses and accelerating bone regrowth in treated areas.

EXAMPLE 5

Treatment of Periodontal Lesion and Fibroma

The following experiment was performed to determine whether the pharmaceutical formulation induces osseous metaplasia in residual periodontal ligamentous tissue. A 38 year-old male subject was diagnosed with a well circumscribed, non-tender, radiolucent lesion at a tooth (location 32) that was the site of a previous wisdom tooth extraction. The history and radiological presentation were consistent with a fibroma. Prior to biopsy, 1 cc of one example of the pharmaceutical formulation having Formulation B from Example 3 above was injected into the lesion with a trochar needle. Repeated radiographs three weeks later showed increased radio-density inside the lesion. Excisional biopsy after treatment confirmed the presence of induced osteoid metaplasia, irregular trabeculae of woven bone, and osteoblastic reaming in a benign fibrous lesion. These results indicate that the pharmaceutical formulation is effective at inducing osteoid metaplasia at the site of a periodontal fibroma.

EXAMPLE 6

Treatment of Compound Fracture

A 25 year-old male sustained a compound comminuted fracture of the right humerus in a motorcycle racing accident. An open surgical reduction with multiple screws and plate fixation was performed the same day as the trauma. Radiographic evidence documented the severity of the injury, with wide gaps in the apposition of bone, despite fixation. One month after the surgery, no healing reaction was evident radiologically. The subject was administered one example of the pharmaceutical formulation having Formulation B from Example 3 above intravenously in four sessions over a two week period. Radiographs taken after treatment and seven weeks after the initial surgical repair showed accelerated repair across multiple gaps in the fracture line. The normal sequence of repair for this type of injury was estimated at four months. Thus, the results indicate that the pharmaceutical formulation is effective at inducing bone regrowth and accelerating the repair of a compound fracture.

EXAMPLE 7

Treatment of Equine Bone Fracture and Joint Damage

Two horses with lameness were treated with examples of the pharmaceutical formulation.

The first horse, a three year-old thoroughbred, was diagnosed with a non-displaced scapular fracture after it showed lameness and failed to respond to conservative measures for one week. One example of the pharmaceutical formulation having Formulation B from Example 3 above was directly injected under fluoroscopic control into the fracture line and the limb was splinted. Within six weeks, the fracture healed without callous or deformity, as shown radiographically. The horse returned to racing eight weeks after the treatment. The normal equine healing time for such a weight-bearing bone fracture is five months for a closed reduction.

The second horse, a six year-old quarterhorse, demonstrated lameness and was diagnosed with a sequestrum of infectious etiology in the carpal bones of its right hind limb. Arthrodesis with screw fixation was perfomed in two carpal joints. One carpal joint was also treated with one example of the pharmaceutical formulation having Formulation B from Example 3 above, which was injected intraoperatively directly into the joint. One carpal joint was not injected with the pharmaceutical formulation and served as a control. Radiographs at three and six weeks after the operation showed accelerated joint fusion in the joint treated with the pharmaceutical formulation, compared to the untreated control joint. The cast was removed from the treated joint at six weeks, almost five months faster than with routine equine arthrodesis procedures.

REFERENCES CITED

The following U.S. Patent documents and publications are hereby incorporated by reference.

U.S. Patents

U.S. Pat. No. 4,451,480 to DeVillez
U.S. Pat. No. 4,591,602 to DeVillez
U.S. Pat. No. 4,983,637 to Herman
U.S. Pat. No. 5,086,076 to Herman
U.S. Pat. No. 5,126,376 to Herman
U.S. Pat. No. 5,190,977 to Herman
U.S. Pat. No. 5,190,979 to Herman
U.S. Pat. No. 5,260,342 to Herman
U.S. Pat. No. 5,270,344 to Herman
U.S. Pat. No. 5,364,879 to Herman

Other Publications

Beck-Coon, R. J., Newton, C. W., Kafrawy, A. H. An in vivo study of the use of a nonresorbable ceramic hydroxyapatite as an alloplastic graft material in periapical surgery. *Oral Surg Oral Med Oral Pathol* vol. 71(4), pp. 483-88, 1991.

Chakraborti, T., Das, S., et al. Oxidant, mitochondria and calcium: an overview. *Cell Signal* vol. 11(2), pp. 77-85, 1999.

Granchi, D., Stea, S., Ciapetti, G., et al. Endodontic cements induce alterations in the cell cycle of in vitro cultured osteoblasts. *Oral Surg Oral Med Oral Pathol Oral Radiol Endod* vol 79(3), pp. 359-66, 1995.

Plachot, J. J., Thil, C. L., et al. Mitochondrial calcium and bone mineralization in the rat fetus. *Bone Miner* vol. 1(2), pp. 157-66, 1986.

World Health Organization, *The Burden of Musculoskeletal Conditions at the Start of the New Millenium, Global Burden of Diseases* 2000 *Study,* 2000.

What is claimed is:

1. A method for stimulating bone regeneration in a patient, comprising:
    administering to the patient an effective amount of a pharmaceutical formulation comprising:
        peroxidic species or reaction products resulting from oxidation of menthol or an alkene by an oxygen-containing oxidizing agent, wherein the oxygen-containing oxidizing agent is selected from the group consisting of singlet oxygen, oxygen in its triplet state, superoxide anion, periodate, hydroxyl radical, hydrogen peroxide, alkyl peroxide, carbamyl peroxide, benzoyl peroxide, oxygen bound to a transition element, and ozone, and wherein the alkene is selected from the group consisting of terpineol, citronellol, nerol, linalool, phytol, geraniol, perillyl alcohol, menthol, geranylgeraniol and farnesol, and wherein the peroxidic species or reaction products resulting from oxidation of menthol or the alkene is from about 0.001% to about 30% by weight of the pharmaceutical formulation;
        a penetrating solvent, wherein the penetrating solvent is selected from the group consisting of dimethylsulfoxide, sterol, lecithin, propylene glycol, and methylsulfonylmethane, and wherein the penetrating solvent is from about 50% to about 99% by weight of the pharmaceutical formulation;
        a dye containing a chelated divalent or trivalent metal, wherein the dye is selected from the group consisting of porphyrin, rose bengal, chlorophyllin, hemin, corrins, texaphrin, methylene blue, hematoxylin, eosin, erythrosin, lactoflavin, anthracene dye, hypericin, methylcholanthrene, neutral red, phthalocyanine, fluorescein, eumelanin, and pheomelanin, and wherein the dye is from about 0.1% to about 30% by weight of the pharmaceutical formulation; and
        an aromatic redox compound, wherein the redox compound is selected from the group consisting of substituted or unsubstituted benzoquinone, naphthoquinone, and anthroquinone, and wherein the aromatic redox compound is from about 0.01% to about 20% by weight of the pharmaceutical formulation.

2. The method of claim 1, wherein the alkene is in a liquid form, in a solution, or in a dispersion.

3. The method of claim 1, wherein the alkene is contained in a fixed oil, an ester, a fatty acid, or an ether.

4. The method of claim 1, wherein the penetrating solvent is a liquid, micelle membrane, liposome, emollient, or vapor.

5. The method of claim 1, wherein the penetrating solvent is dimethylsulfoxide ("DMSO").

6. The method of claim 1, wherein the dye is selected from the group consisting of porphyrin, rose bengal, chlorophyllin, and a mixture thereof.

7. The method of claim 1, wherein the metal is iron.

8. The method of claim 1, wherein the metal is selected from the group consisting of copper, manganese, tin, magnesium, and strontium.

9. The method of claim 1, further comprising an electron donor.

10. The method of claim 9, wherein the electron donor is ascorbic acid or a pharmaceutical salt thereof.

11. A method for stimulating bone regeneration in a patient, comprising:
    administering to the patient an effective amount of a pharmaceutical formulation comprising:
        peroxidic species or reaction products resulting from oxidation of geraniol by a mixture of ozone and oxygen;
        dimethylsulfoxide ("DMSO");
        a dye containing a chelated divalent or trivalent metal, wherein the dye comprises a mixture of hematoporphyrin and rose bengal or a mixture of hematoporphyrin and chlorophyllin; and
        methylnaphthoquinone.

12. A method for increasing osteoblastic activity in a patient, comprising:
    administering to the patient an effective amount of a pharmaceutical formulation comprising:
        peroxidic species or reaction products resulting from oxidation of menthol or an alkene by an oxygen-containing oxidizing agent, wherein the oxygen-containing oxidizing agent is selected from the group consisting of singlet oxygen, oxygen in its triplet state, superoxide anion, periodate, hydroxyl radical, hydrogen peroxide, alkyl peroxide, carbamyl peroxide, benzoyl peroxide, oxygen bound to a transition element, and ozone, and wherein the alkene is selected from the group consisting of terpineol, citronellol, nerol, linalool, phytol, geraniol, perillyl alcohol, menthol, geranylgeraniol and farnesol, and wherein the peroxidic species or reaction products resulting from oxidation of menthol or the alkene is from about 0.001% to about 30% by weight of the pharmaceutical formulation;
        a penetrating solvent, wherein the penetrating solvent is selected from the group consisting of dimethylsulfoxide, sterol, lecithin, propylene glycol, and methylsulfonylmethane, and wherein the penetrating solvent is from about 50% to about 99% by weight of the pharmaceutical formulation;
        a dye containing a chelated divalent or trivalent metal, wherein the dye is selected from the group consisting of porphyrin, rose bengal, chlorophyllin, hemin, corrins, texaphrin, methylene blue, hematoxylin, eosin, erythrosin, lactoflavin, anthracene dye, hypericin, methylcholanthrene, neutral red, phthalocyanine, fluorescein, eumelanin, and pheomelanin, and wherein the dye is from about 0.1% to about 30% by weight of the pharmaceutical formulation; and
        an aromatic redox compound, wherein the redox compound is selected from the group consisting of substituted or unsubstituted benzoquinone, naphthoquinone, and anthroquinone, and wherein the aromatic redox compound is from about 0.01% to about 20% by weight of the pharmaceutical formulation.

13. The method of claim 12, wherein the alkene is in a liquid form, in a solution, or in a dispersion.

14. The method of claim 12, wherein the alkene is contained in a fixed oil, an ester, a fatty acid, or an ether.

15. The method of claim 12, wherein the penetrating solvent is a liquid, micelle membrane, liposome, emollient, or vapor.

16. The method of claim 12, wherein the penetrating solvent is dimethylsulfoxide ("DMSO").

17. The method of claim 12, wherein the dye is selected from the group consisting of porphyrin, rose bengal, chlorophyllin, and a mixture thereof.

18. The method of claim 12, wherein the metal is iron.

19. The method of claim 12, wherein the metal is selected from the group consisting of copper, manganese, tin, magnesium, and strontium.

20. The method of claim 12, further comprising an electron donor.

21. The method of claim 19, wherein the electron donor is ascorbic acid or a pharmaceutical salt thereof.

22. A method for increasing osteoblastic activity in a patient, comprising:
   administering to the patient an effective amount of a pharmaceutical formulation comprising:
   peroxidic species or reaction products resulting from oxidation of geraniol by a mixture of ozone and oxygen;
   dimethylsulfoxide ("DMSO");
   a dye containing a chelated divalent or trivalent metal, wherein the dye comprises a mixture of hematoporphyrin and rose bengal or a mixture of hematoporphyrin and chlorophyllin; and
   methylnaphthoquinone.

* * * * *